US008278081B2

(12) United States Patent
Schmidt

(10) Patent No.: US 8,278,081 B2
(45) Date of Patent: Oct. 2, 2012

(54) METHOD FOR PRODUCING NON-INFECTIOUS PRODUCTS FROM INFECTIOUS ORGANIC WASTE MATERIAL

(75) Inventor: Erick Schmidt, Ponoka (CA)

(73) Assignee: Biosphere Technologies, Inc., Ponoka, Alberta (CA)

( * ) Notice: Subject to any disclaimer, the term of this patent is extended or adjusted under 35 U.S.C. 154(b) by 736 days.

(21) Appl. No.: 12/273,794

(22) Filed: Nov. 19, 2008

(65) Prior Publication Data

US 2009/0130733 A1 May 21, 2009

Related U.S. Application Data

(60) Provisional application No. 60/989,259, filed on Nov. 20, 2007.

(51) Int. Cl.
*A62D 3/40* (2007.01)
*A62D 3/02* (2007.01)
*C12P 5/02* (2006.01)
*A61K 38/01* (2006.01)

(52) U.S. Cl. ............. 435/167; 435/262.5; 530/407; 71/11

(58) Field of Classification Search .......... 422/28; 71/11; 588/249; 435/167, 262.5; 530/407
See application file for complete search history.

(56) References Cited

U.S. PATENT DOCUMENTS

| | | | |
|---|---|---|---|
| 3,385,687 A | 5/1968 | Brown | |
| 3,442,637 A | 5/1969 | Hudson et al. | |
| 3,533,775 A | 10/1970 | Brown | |
| 3,635,409 A | 1/1972 | Brewer | |
| 4,201,128 A | 5/1980 | Whitehead et al. | |
| 4,271,326 A | 6/1981 | Mego | |
| 4,285,719 A | 8/1981 | Criss | |
| 4,487,699 A | 12/1984 | Long, Jr. | |
| 4,582,612 A | 4/1986 | Long, Jr. | |
| 4,586,659 A | 5/1986 | Easter, II | |
| 4,659,464 A | 4/1987 | Long, Jr. | |
| 4,695,388 A | 9/1987 | Long, Jr. | |
| 4,877,531 A | 10/1989 | Burkett | |
| 5,147,563 A | 9/1992 | Long, Jr. et al. | |
| 5,250,100 A | 10/1993 | Armbristor | |
| 5,422,074 A | 6/1995 | Schmidt | |
| 5,772,721 A | 6/1998 | Kazemzadeh | |
| 5,783,081 A | 7/1998 | Gaddy | |
| 5,853,450 A | 12/1998 | Burnham et al. | |
| 6,022,394 A | 2/2000 | Paananen et al. | |
| 6,197,081 B1 | 3/2001 | Schmidt | |
| 2007/0197852 A1 | 8/2007 | Wilson et al. | |

FOREIGN PATENT DOCUMENTS

| | | |
|---|---|---|
| AU | 2008328482 A1 | 5/2009 |
| CA | 1029978 | 4/1978 |
| CA | 1147572 | 6/1983 |
| CA | 1161577 | 1/1984 |
| CA | 2054841 A1 | 5/1993 |
| CA | 2420064 A1 | 2/2002 |
| CA | 2492034 A1 | 1/2004 |
| EP | 1716920 A1 | 11/2006 |
| JP | 2005-103539 A | 4/2005 |
| RU | 2143473 C1 | 12/1999 |
| WO | 9308849 | 5/1993 |
| WO | 9529884 | 11/1995 |
| WO | 9947282 A1 | 9/1999 |
| WO | 0215945 A1 | 2/2002 |
| WO | 2004004936 A2 | 1/2004 |
| WO | 2005077514 A1 | 8/2005 |

OTHER PUBLICATIONS

Office Action Issued Apr. 27, 2011 in RU Application No. 2010125227.
Int'l Preliminary Report on Patentability Issued Feb. 24, 2010 in Int'l Application No. PCT/CA2008/002030.
Int'l Search Report Issued Feb. 12, 2009 in Int'l Application No. PCT/CA2008/002030; Written Opinion.
Office Action issued Jun. 28, 2011 in JP Application No. 2010-534327 (English translation).
Examination Report issued Feb. 16, 2011 in NZ Application No. 586219.
Office Action issued Nov. 22, 2011 in KR Application No. 10-2010-7013657.
Office Action issued Jun. 22, 2012 in RU Application No. 2010125227/15.
Search Report issued Jun. 21, 2012 in EP Application No. 08852053.1.
Somerville et al, "Inactivation of a TSE agent by a novel biorefinement system", Process Biochemistry, vol. 44, No. 9, pp. 1060-1062 (2009).

*Primary Examiner* — Chih-Min Kam
(74) *Attorney, Agent, or Firm* — Panitch Schwarze Belisario & Nadel LLP

(57) ABSTRACT

A method for producing a hydrolyzed, sterile, denatured product from infectious organic waste material includes (a) introducing, into a reactor capable of being heated and pressurized, infectious organic waste material to form a reaction mixture; (b) subjecting the reaction mixture to saturated steam at a temperature and pressure within the reactor for a duration of time sufficient to thermally hydrolyze and denature the reaction mixture into a denatured slurry; and (c) alternatively (1) anaerobically digesting the denatured slurry, or (2) fractionating the denatured slurry based on molecular weight, density and size into at least two hydrolyzed, sterile, denatured products. The resulting hydrolyzed, sterile products have safe and valuable nutritional properties and may be used in a wide range of commercial, agricultural, and industrial products or processes.

19 Claims, No Drawings

METHOD FOR PRODUCING NON-INFECTIOUS PRODUCTS FROM INFECTIOUS ORGANIC WASTE MATERIAL

CROSS-REFERENCE TO RELATED APPLICATION

This application claims the benefit under 35 U.S.C. §119(e) of U.S. Provisional Patent Application No. 60/989,259, filed Nov. 20, 2007, the entire disclosure of which is hereby incorporated by reference herein.

BACKGROUND OF THE INVENTION

The increase in major infectious diseases threatening human and animal health has led to new international regulations and laws which prohibit the use of carcasses, animal by-products, food waste and other certain specified risk material (SRM) as defined in various jurisdictions for use as feed for animals, and as feedstock for rendering plants which convert these materials into meat and bone meal (MBM) and other animal nutrient products (fats and blood meal, etc). The onset of the new transmissible spongiform encephalopathies (TSEs) or prion diseases, such as bovine spongiform encephalopathy (BSE), chronic wasting disease (CWD), and scrapie, as well as the emerging viral diseases in poultry and other animals, has created serious problems regarding the disposal or recycling of these materials, to assure that they are eliminated from human and animal food chains. Traditional rendering does not create conditions to denature these highly resistant disease agents, and traditional disposal by burial and composting does not destroy the most resistant pathogens (BSE, anthrax, etc.). Furthermore, incineration of large amounts of these carcass, food and other wastes creates secondary environmental pollution and toxic compounds.

There presently exists a challenge to develop a technology that safely eliminates the health and environmental risks created by these infectious or potentially infectious organic materials, without the negative impacts of pollution and odors associated with traditional methods of burial and burning. The ideal solution would be the conversion and refinement of meat, bone, fat and fiber materials derived from waste or condemned animal and plant sources, so that the disease agents are destroyed, without destroying the primary beneficial components, such as nutrient elements of amino acids, fatty acids and minerals. These beneficial components can then be reformed into safe, valuable nutrient products, especially for fertilizers and feedstock nutrients and for anaerobic digesters creating methane biogas for co-generation of electricity and steam. The present invention provides such a solution.

BRIEF SUMMARY OF THE INVENTION

The present invention effectively addresses the problem of treatment and environmentally safe disposal of organic waste material through a bio-refining process which transforms infectious material, such as waste household foods, waste meat and bone residuals from food processing industries, dead and diseased animal carcasses from all sources, dewatered sewage sludge, SRM, animal by-products (ABP), and other solid and liquid organic waste, into denatured, value-added products.

The present invention relates to a method for producing a hydrolyzed, sterile, denatured product from infectious organic waste material, the method comprising (a) introducing, into a reactor capable of being heated and pressurized, infectious organic waste material to form a reaction mixture; (b) subjecting the reaction mixture to saturated steam at a temperature and pressure within the reactor for a duration of time sufficient to thermally hydrolyze and denature the reaction mixture into a denatured slurry; and (c) alternatively (1) anaerobically digesting the denatured slurry, or (2) fractionating the denatured slurry based on molecular weight, density and size into at least two hydrolyzed, sterile, denatured products.

DETAILED DESCRIPTION OF THE INVENTION

In general, this invention relates to the treatment of infectious organic waste material, including SRM, ABP, human, animal and plant waste materials, such as food wastes and food processing wastes from household and food services businesses; diseased plants, such as those affected by fungal diseases; residual meat and bones from meat and fish packers; livestock, poultry and pet carcasses from farm, feedlots, slaughter houses, and veterinarian clinics; and classified or condemned animal carcasses, body parts, organs and tissues which may be specified by national, regional or community disease and control programs for destruction; animal offal; municipal solid waste containing such waste; and sewage sludge from wastewater treatment plants; as well as any combination or mixture of any of these materials. The treatment of such infectious organic waste material according to this invention denatures the material, rendering it non-infectious.

As used herein, the term "infectious organic waste material" means organic waste material which is actually or potentially infectious, in that it actually or potentially includes any type of pathogenic agent that is capable of causing illness or disease in a human or an animal, including but not limited to the types set forth in the immediately preceding paragraph. Thus, the term includes organic waste materials that are expected or suspected to be infectious by virtue of some samples of other batches or general types of such materials having been found to contain pathogens. It is not necessary that the material being treated actually be tested in advance to determine whether or not it is actually infectious, and therefore, the infectious organic waste material may not be actually infectious. Typically, such organic waste material is by regulation or tradition inedible.

As used herein, the term "denature" and its grammatical equivalents, means both to sterilize and to inactivate pathogenic agents such that they are no longer harmful to humans or animals. This term is chosen for use herein as applying to microorganisms, such as fungi, bacteria or other microorganisms capable of metabolism and reproduction on their own; viruses which may be viewed as either extremely simple microorganisms or as extremely complex molecules that typically contain a protein coat surrounding an RNA or DNA core of genetic material but no semipermeable membrane, that are capable of growth and multiplication only in living cells; and also TSEs or prions, such as BSE, CWD and scrapie, which are proteins, rather than microorganisms, but nonetheless interact with human and animal biochemicals to form a template or pattern which causes illness or disease. Thus, the term "denature" is used herein as a term which encompasses rendering any of these harmful pathogenic agents not harmful according to the method of the present invention, regardless of whether the pathogenic agent is rendered not harmful by sterilization, inactivation, thermal hydrolysis or any other technique within the method of the present invention.

As used herein, the term "hydrolyzed, sterile product" includes any beneficial product, such as amino acids, fatty acids, minerals and fibrous or non-fibrous organic nutrient substances, which result from the denaturing process of the present invention.

As used herein, "animal by-product" (ABP) means any animal-derived material not intended for human consumption, whether or not it is infected with any infectious agent, that is or may be regulated by any government or government agency or government organization, such as European Union Regulation EC 1774/2002 of the European Parliament and the European Council that was adopted Oct. 3, 2002, the Statutory Instrument 2005 No. 2347 Animal By-Products Regulations 2005 in England, and others. Such ABPs include, for example, parts of a slaughtered animal that are not directly consumed by humans, including dead on-farm animals and catering waste (waste food originating from restaurants, catering facilities and kitchens) that contains or has been in contact with meat products, whether cooked or uncooked, some of which may be used in animal proteins like meat-meal, bone-meal, fats, gelatin, collagen, pet food and other technical products, such as glue, leathers, soaps, fertilizers, etc.

As used herein, the term "specified risk material" (SRM) means any material that is the type that is, or may be, or is susceptible of being, infected with any infectious agent, such as BSE and scrapie, and that is or may be regulated by any government or government agency or government organization, such as Interim Final Rule of the U.S. Department of Agriculture, Food Safety Inspection Service, published in the Federal Register of Jan. 12, 2004, at page 1862 et seq., the European Union Community TSE Regulation 9999/2001, and the Canadian Food Inspection Agency regulations effective Aug. 23, 2003. Such SRMs include, for example, for cattle: tonsils, intestines, skull excluding the mandible but including the brain and eyes and spinal cord, vertebral column with certain exceptions, and the dorsal root ganglia; and for sheep and goats, the spleen and ileum and skull, including the brains and eyes.

As used herein, the term "substantial absence of extraneous fibers, oxidizing agents, or acid or alkaline compounds," means that such fibers, oxidizing agents or acid or alkaline compounds are not intentionally added separately or in combination together to the reaction mixture in an amount that affects the resulting denatured product. However, such fibers, oxidizing agents or acid or alkaline compounds may incidentally be included as minor materials with the infectious organic waste material that forms the reaction mixture, such as corrugated cardboard packaging typically containing at least some of the infectious organic waste, on the order of no more than about 2 wt % of the reaction mixture.

As used herein, the singular includes the plural and the plural includes the singular, unless otherwise specifically stated or clear from the context.

The hydrolyzed, sterile, denatured product produced in the invention can be employed directly after denaturation, or after fractionation in agricultural, industrial and commercial applications, such as fertilizers, soil conditioners and animal feed ingredients, as well as in anaerobic digesters (AD) to produce biogas (primarily methane) which may be used as an energy source for co-generating electricity, steam, hot water or for use in any other fuel applications. The use of the hydrolyzed, sterile product of the present invention directly, and particularly the carbon-rich fibrous and fatty acid fractions after fractionation, in AD vessels is highly efficient, since it has already been hydrolyzed. Because the first phase of anaerobic digestion produces a hydrolyzed material, starting with such a material reduces the process times in the AD vessels, and increases the efficiency of methane biogas generation.

While any type of infectious organic waste material may be treated using this invention, it is particularly effective for treating animal waste, including ABPs, which include lipids in amounts on the order of up to about 30 wt %, and typically about 15 to about 30 wt %.

Animal carcasses, body parts, organs or tissues which may be treated according to the present invention include those of typical livestock including cattle, sheep, goats, hogs, pigs, horses, and poultry including chickens, geese, and ducks, domestic pet animals, such as dogs and cats, zoo animals, and virtually any other animal from any sources whose carcass, body parts, organs or tissues must be disposed.

It is preferred that the infectious organic waste material to be treated effectively according to the present invention be introduced into a suitable reactor or vessel in the substantial absence of extraneous fibers, oxidizing agents, or acid or alkaline compounds. However, as noted above, some of such extraneous fibers, oxidizing agents, or acid or alkaline compounds may be present incidentally as part of the infectious organic waste material that is delivered for treatment according to the present invention.

The infectious organic waste material to be treated effectively according to the present invention, resulting in denatured product fractions, may be introduced into a suitable reactor or vessel in the form in which its components are received from a source, such as a slaughter house, processing plant or other source. Typically, the infectious organic waste material is received for treatment in the form of whole or somewhat broken skulls, vertebral columns, large and small bones, defatted meat and bone materials, and other components, typically, but not necessarily with flesh and fat attached, and without having been comminuted to smaller particles. The thermal hydrolysis treatment of the present invention is sufficient to denature such infectious organic waste material from various sources, regardless of the size of such source materials.

It is preferred that the infectious organic waste material, which may contain any or all of the previously mentioned materials, is comminuted, such as by grinding or shredding into particles of a desired size to form a reaction mixture, more specifically to facilitate efficient and uniform heat and steam penetration into the particles. The comminuting may be done using any suitable equipment, such as pre-breaker grinders, crushers, hammer mills or shear shredders. Comminuting should be done in an enclosed environment to avoid aerosol pathogen emissions into the outside environment. The preferred comminuting is done until the reaction mixture has a size sufficient to facilitate and enhance heat and steam penetration such that the infectious organic waste material is substantially uniformly denatured. Comminuting the material also makes handling it more efficient, since comminuted material may be conveyed more easily into and out of the reactor, such as by pumping, as the infectious waste material usually includes sufficient liquid, typically water, to be pumpable. Comminution also increases the packing density within the reactor, and allows for faster processing due to the smaller particles and increased surface area subjected to thermal hydrolysis, compared to larger particles or pieces of material being treated. The specific size of the particles depends on the density, type and nature of material being comminuted, but generally, the material is comminuted sufficiently if the size is reduced to a maximum largest dimension of up to about 50 mm, and more preferably about 20 mm to about 50 mm in the maximum largest dimension.

The resulting reaction mixture, i.e., the infectious organic waste material, and preferably after it has been comminuted to a desired particle size, preferably, but not necessarily, is prepared in the substantial absence of any extraneous acid or alkaline chemicals, extraneous oxidizing agents or extraneous fibrous material, such as additional absorbent or adsorbent fibrous material, as explained above.

The resulting reaction mixture is transferred, such as by pumping, into a reactor or vessel designed to allow sufficient interaction of reaction mixture with heated and pressurized saturated steam, such as a batch or continuous process hyperbaric mixing reactor with at least one shaft having radially offset mixing paddles extending from the shaft, or a rotating and or oscillating vessel with internal offset fixed flanges. Other suitable batch or continuous process reactors or mixing vessels could be used. The reaction mixture is heated in the reactor with saturated steam at an elevated temperature and super-atmospheric pressure for a time sufficient to thermally hydrolyze the mixture, in the absence of additional extraneous acid or alkaline chemicals, in the absence of additional extraneous oxidizing agents and in the absence of additional extraneous fibrous material, such as additional absorbent or adsorbent fibrous material. Suitable preferred conditions for denaturing the reaction mixture include heating to a temperature of about 150° C. to about 200° C., more preferably about 180° C., and pressurizing to a pressure of about 5 bar (about 72.5 pounds per square inch (psi)) to about 15 bar (about 217.8 psi), more preferably about 10 bar (about 145 psi) to about 13 bar (about 188.5 psi), for a duration of time of about 20 minutes to about 60 minutes, more preferably for about 40 minutes. Such conditions ensure the destruction of infectious agents, including spore forming bacteria and prions, by denaturing the tertiary structures of the prions or protein and destroying the infectious functional nature of the pathogenic agents. The high temperature saturated steam breaks down the molecular bonds of the protein, carbohydrates, fats, and mineral compounds, hydrolyzing and denaturing the original molecular structures to primary forms of beneficial products, such as amino acids, fatty acids, sugars, lignans, cellulose and minerals, into a resulting aqueous slurry that is largely organic, incorporating water naturally present in the organic waste material, as well as the injected steam.

Following exposure of the reaction mixture in the reactor vessel to the high temperature and pressure treatment for a time sufficient to denature the reaction mixture, the reactor vessel is preferably depressurized and the resulting denatured slurry preferably is transferred to a holding tank before further processing.

Upon denaturation, the waste organic material that has been converted to the denatured slurry has a target infectivity reduction of $ID_{50}$ of a minimum of 4 logs. Infectivity is a measure of the ability of a disease agent to establish itself in the host. Attempts to quantify infectivity typically involve the use of $ID_{50}$, which is the individual dose or numbers of the agent required to infect 50% of a specified population of susceptible subjects under controlled environmental conditions The factor "4 logs" means that the amount of infectious material is reduced by four orders of magnitude equal to $1 \times 10^4$, or 10,000.

The denatured slurry can then be used directly or preferably after fractionation into more specific liquid or dehydrated products for various uses, including, for example and without limitation, agricultural, industrial and commercial applications, such as fertilizers, soil conditioners and animal feed ingredients, as well as in anaerobic digesters (AD) to produce biogas (primarily methane) which may be used as an energy source for co-generating electricity, steam or hot water or for any other fuel applications. As noted above, when used in ADs, the denatured organic slurry can be used directly before fractionation or after fractionation. Preferably, after fractionation, the fibrous and fatty acid fractions can be used in ADs. Other fractions may be used for other products, such as amino acids and minerals for animal feed, fertilizers, bone meal, nutriceutical compositions, and materials for soil reclamation, remediation and conditioning, as well as many other uses.

The denatured slurry is preferably fractionated based on the molecular weight, density and particle size of its various components. Fractionation may be performed using high speed centrifuges to achieve classification of various products. For example, an industrial decanter centrifuge, such as those available from Alfa Laval, based in Sweden with offices or distribution centers in over fifty countries, may be used that is capable of continuously separating the slurry into solid and liquid fractions. Speeds of up to about 4000 revolutions per minute (rpm) create up to about 2500 gravitational (G) force, causing solids, such as fibrous lignans, cellulose and minerals, to separate from the liquid fraction, resulting in a semi-dry or semi-moist fibrous material. Such fibrous material is mostly made of "paunch manure" from the animals' stomachs, other grain and feed residues in the small and large intestines of the animals and any commingled or other vegetable or fruit fibers.

The decanted liquid fraction generally has a brown color and an average solid content of less than about 3 wt %. Containing mostly water, fatty acids, denatured proteins (amino acids), dissolved minerals and other organic residues, this liquid fraction may be further fractionated using a disc stack centrifuge, such as those manufactured by Alfa Laval. Revolving at up to about 4000 to 5000 rpm and creating up to about 5000 G force, a disk stack centrifuge is typically calibrated to classify the liquid stream into three fractions—a lightweight and less dense fatty acid solution, a heavier and higher density amino acid/mineral solution, and a solid, heavy and most dense mineral fines paste. The lighter weight, less dense fatty acid solution moves to the top section of the centrifuge where it is discharged. The heavier and more dense stream incorporating amino acids, water, glycerol, and dissolved minerals, flows to a lower port. Fine solids, typically the heaviest and most dense sediments incorporating minerals, accumulate at the base of the centrifuge.

Additional liquid-liquid separations or dehydration of solid and liquid fractions, for example, to concentrate amino acids, may be further undertaken to develop specific industrial, commercial, or agricultural products. For example, dehydration results in stable, transportable nutrient products. The fractionated hydrolyzed, sterile products, preferably the carbon-rich fibrous and fatty acid fractions could also be used in digesters to produce biogas which may be used as an or the source of energy for co-generating electricity or steam or as a source of biomethane for natural gas pipeline distribution or for compression into liquefied natural gas (LNG) for any suitable use, such as domestic, commercial, industrial or vehicular fuel.

The invention will now be described in more detail with reference to the following specific, non-limiting example.

EXAMPLE

Sample Hydrolysis and Fractionation of Infectious Animal By-Product and Organic Waste Material

| Sample Composition | |
|---|---|
| 20 kg | dead whole chickens |
| 60 kg | packing plant vertebral column and trim bones |
| 73 kg | beef skulls and hooves |
| 61 kg | inedible beef organs, intestinal tissue, stomach paunch manure, and pig skulls |
| 52 kg | comingled waste vegetables and food scraps and cardboard packaging containing them |
| 37 kg | water |

Thermal Hydrolysis Processing

The above material was thermally hydrolyzed in a 1000 liter BioRefinex™ high pressure reactor designed as a test system for Biosphere Technologies Inc. of Edmonton, Alberta. The reactor vessel was preheated by steam jacket piping. The above material was loaded through the top hatch of the reactor vessel and steam heated in the vessel to a temperature of 180° C. and a pressure of 12.4 bar (180 psi), and subjected to these parameters for a period of 40 minutes while being agitated by internal shaft and paddles rotating at 30 rpm within the reactor vessel.

Following the thermal hydrolysis cycle, the vessel was depressurized and the steam was vented to a condenser system. At ambient pressure, the material was evacuated from a bottom port of the reactor vessel.

The output denatured material had been transformed into a brown hydrolyzed, sterile, denatured slurry. Although this particular batch of materials were not specifically tested for $ID_{50}$, other batches of similar infectious organic waste material treated as in this Example and according to the present invention as set forth above, were tested by an independent government laboratory with excellent results showing that the method of this invention results in denatured products.

The hydrolyzed slurry was fed into a continuous flow pilot scale decanter centrifuge operating at 2500 G force manufactured by Alfa Laval of Sweden. The system produced two fractions, one comprising a semi-moist solid fibrous material, and the second a clarified liquid material. Table 1 contains the results of an analysis by an independent laboratory of the content of this semi-moist solid fibrous material both as submitted and as dehydrated.

TABLE 1

Analysis of Semi-Moist Solid Fibrous Fraction

| | As Received | As Dehydrated | Method Reference |
|---|---|---|---|
| Physical | | | |
| Ash | 21.22% | 40.88% | AOAC-942.05* |
| Moisture | 48.1% | | AOAC-935.29 |
| Proteins | | | |
| Crude Protein ($TN^1 \times 6.25$) | 17.6% | 34.9% | AOAC-988.05 |

TABLE 1-continued

Analysis of Semi-Moist Solid Fibrous Fraction

| | As Received | As Dehydrated | Method Reference |
|---|---|---|---|
| Fibers | | | |
| Crude Fibers | 4.8% | 9.3% | AOAC-962.09 |
| Fats | | | |
| Total Fat | 5.82% | 11.21% | |
| Calculated Values | | | |
| Nitrogen Free Extract | | 4.6% | |
| TDN (Crude)$^2$ | 27.17% | 52.35% | |
| DE (Crude)$^3$ | 1.37 Mcal/kg | 2.63 Mcal/kg | |
| GE$^4$ | 1.91 Mcal/kg | 3.67 Mcal/kg | |
| ME$^5$ | 1.24 Mcal/kg | 2.39 Mcal/kg | |
| NEF$^6$ | 0.78 Mcal/kg | 1.51 Mcal/kg | |
| Minerals | | | |
| Calcium | 7.08% | 13.6% | AOAC-985.01 |
| Phosphorus | 3.44% | 6.63% | AOAC-985.01 |
| Potassium | 0.13% | 0.25% | AOAC-985.01 |
| Magnesium | 0.12% | 0.22% | AOAC-985.01 |
| Sodium | 0.27% | 0.52% | AOAC-985.01 |
| Salt | 0.69% | 1.33% | AOAC-985.01 |

Notes:
*AOAC is AOAC International, founded in 1884 as the Associations of Official Agricultural Chemists, later changed to the Association of Official Analytical Chemists, and since 1992, AOAC International.
$^1$Total Nitrogen
$^2$Total Digestible Nutrients
$^3$Digestible Energy
$^4$Gross Energy
$^5$Metabolizable Energy
$^6$Net Energy of Feed The liquid fraction was fed into the inlet pipe of a continuous flow pilot scale disc stack centrifuge, operating at 4000 G force, manufactured by Alfa Laval of Sweden. This centrifuge produced two liquid streams. The lighter fraction contained fatty acids having the analysis set forth in Table 2, and the heavier fraction including amino acids having the analysis set forth in Table 3 and a heavy solid mineral fines fraction, having the analysis set forth in Table 4. The analyses yielding the results in Tables 2 through 4 were done by the same independent laboratory that did the analysis for Table 1.

TABLE 2

Fatty Acid Fraction

| | As Received | As Dehydrated | Method Reference |
|---|---|---|---|
| Physical | | | |
| Moisture | 45.1% | | AOAC-935.29 |
| Misc | | | |
| Free Fatty Acid | 6.2% | 11.3% | AOCS-Ca 5B-71* |

*AOCS is American Oil Chemists' Society

TABLE 3

Amino Acid and Related Fraction

| Amino Acid or Related Compound | Wt % |
|---|---|
| Aspartate | 0.745 |
| Threonine | 0.434 |
| Serine | 0.317 |
| Glutamine | 1.405 |
| Proline | 1.129 |
| Glysine | 1.917 |
| Alanine | 0843 |

TABLE 3-continued

Amino Acid and Related Fraction

| Amino Acid or Related Compound | Wt % |
|---|---|
| Cystine* | 0.022 |
| Valine | 0.501 |
| Methionine* | 0.146 |
| Isoleucine | 0.258 |
| Leucine | 0.59 |
| Tyrosine | 0.221 |
| Phenylalanine | 0.359 |
| Histidine | 0.213 |
| Lysine | 0.485 |
| Ammonia | 0.241 |
| Arginine | 0.634 |
| Tryptophan | 0.048 |

*Cystine and Methionine determined by oxidized procedure

TABLE 4

Mineral Fines Fraction

| Minerals, Nitrogen & Misc. | Amount |
|---|---|
| Moisture @ 104° C. | 83.76 Wt % |
| Total Nitrogen* | 2.20 Wt % |
| Total $P_2O_5$ | 0.689 Wt % |
| Soluble $K_2O$ | 0.22 Wt % |
| Total Sulfur* | 0.10 Wt % |
| Boron | 7 ppm |
| Calcium | 425 ppm |
| Cobalt | <0.5 ppm |
| Copper | 2.5 ppm |
| Iron | 97.8 ppm |
| Magnesium | 207 ppm |
| Manganese | 0.7 ppm |
| Molybdenum | <0.5 ppm |
| Sodium | 1420 ppm |
| Zinc | 1.5 ppm |

*Nitrogen and Sulfur analysis determined by combustion

Based on the analyses provided in the Example, it is clear that the present invention produces valuable denatured fibrous materials, fatty acids, nutrients and minerals useful for animal feed, fertilizer bone meal, nutriceutical compositions, and materials for soil reclamation, remediation and conditioning, as well as many other uses, as well as denatured slurry or fractions for use in anaerobic digestion for production of biogas, with the myriad uses of such biogas.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

I claim:

1. A method for producing hydrolyzed, sterile, denatured organic products from infectious organic waste material, the method comprising:
    (a) introducing, into a reactor capable of being heated and pressurized, infectious organic waste material in the substantial absence of additional extraneous fibers, oxidizing agents, or acid or alkaline compounds, to form a reaction mixture;
    (b) subjecting the reaction mixture to saturated steam at a temperature of about 150° C. to about 200° C. and a pressure of about 5 bar to about 15 bar within the reactor for a duration of time of about 20 minutes to about 60 minutes sufficient to thermally hydrolyze and denature the reaction mixture into a denatured organic slurry; and
    (c) alternatively (1) anaerobically digesting the denatured slurry, or (2) fractionating using centrifugal force the denatured organic slurry into at least two hydrolyzed, sterile, denatured organic products.

2. The method according to claim 1, wherein (c) is anaerobically digesting the denatured slurry to produce biogas.

3. The method according to claim 1, wherein (c) is fractionating the denatured slurry based on molecular weight, density and size into at least two hydrolyzed, sterile, denatured products.

4. The method according to claim 3, further comprising anaerobically digesting at least one of the fractionated products.

5. The method according to claim 4, wherein the at least one fractionated product is at least one of a fibrous fraction and a fatty acid fraction.

6. The method according to claim 1, further comprising, before (a), comminuting the infectious organic waste material into particles of organic material to form a reaction mixture, the particles of organic material having a size up to or about 50 mm in a maximum largest dimension.

7. The method according to claim 6, wherein the comminuted particles of organic material have a particle size of about 20 mm to about 50 mm in a maximum largest dimension.

8. The method according to claim 1, wherein the saturated steam is at a pressure of about 10 bar to about 13 bar.

9. The method according to claim 1, wherein the steam is at a temperature of about 180° C.

10. The method according to claim 1, wherein the reaction mixture is subjected to the saturated steam for a time of about 40 minutes.

11. The method according to claim 1, wherein the denatured organic slurry is fractionated to form a liquid fraction and a solid fraction.

12. The method according to claim 11, wherein the fractionation is accomplished using a decanter centrifuge.

13. The method according to claim 11, wherein the liquid fraction is further fractionated into at least two liquid fractions.

14. The method according to claim 13, wherein the further liquid fractionation is accomplished using a disk stack centrifuge.

15. The method according to claim 1, further comprising dehydrating the denatured organic slurry or at least one of the fractionated products.

16. The method according to claim 1, wherein the infectious organic waste material is animal waste material, plant waste material, waste household foods, waste meat and bone residues from food processing industries or slaughter houses, dead and diseased animal carcasses, animal offal, specified risk material, sewage sludge, or mixtures thereof.

17. A method for producing a hydrolyzed, sterile, denatured product from infectious organic waste material, the method comprising:
    (a) introducing, into a reactor capable of being heated and pressurized, infectious organic waste material to form a reaction mixture;
    (b) subjecting the reaction mixture to saturated steam at a temperature and pressure within the reactor for a duration of time sufficient to thermally hydrolyze and denature the reaction mixture into a denatured slurry; and
    (c) anaerobically digesting the denatured slurry to produce biogas.

18. A method for producing a hydrolyzed, sterile, denatured product from infectious organic waste material, the method comprising:
- (a) introducing, into a reactor capable of being heated and pressurized, infectious organic waste material to form a reaction mixture;
- (b) subjecting the reaction mixture to saturated steam at a temperature and pressure within the reactor for a duration of time sufficient to thermally hydrolyze and denature the reaction mixture into a denatured slurry; and
- (c) fractionating the denatured slurry based on molecular weight, density and size into at least two hydrolyzed, sterile, denatured products;

the method further comprising anaerobically digesting at least one of the fractionated products.

19. The method according to claim 18, wherein the at least one fractionated product is at least one of a fibrous fraction and a fatty acid fraction.

* * * * *